United States Patent [19]

Tamura et al.

[11] Patent Number: 4,501,557
[45] Date of Patent: Feb. 26, 1985

[54] BALANCING DEVICE FOR DENTAL ARM

[75] Inventors: Jun Tamura; Takahiro Matsui, both of Kyoto; Kazuo Hozumi, Shiga, all of Japan

[73] Assignee: Kabushiki Kaisha Morita Seisakusho, Kyoto, Japan

[21] Appl. No.: 516,802

[22] Filed: Jul. 25, 1983

[30] Foreign Application Priority Data

Jul. 26, 1982 [JP]  Japan ............................ 57-113638[U]

[51] Int. Cl.³ ............................................... A61C 1/14
[52] U.S. Cl. ...................................... 433/79; 362/427; 362/804
[58] Field of Search ................. 433/79, 29; 248/289.1; 362/427, 804

[56] References Cited

U.S. PATENT DOCUMENTS

| | | | |
|---|---|---|---|
| 2,547,532 | 4/1951 | Mendelsohn | 362/427 |
| 3,584,793 | 6/1971 | Ilzig | 362/427 |
| 3,764,795 | 10/1973 | Austin, Jr. | 433/29 |
| 3,805,388 | 4/1974 | Kato | 433/79 |

Primary Examiner—John J. Wilson
Attorney, Agent, or Firm—Koda and Androlia

[57] ABSTRACT

The present invention relates to a balancing device for vertically movable dental arms such as a dental light arm and a dental tray arm, and more specifically to a balancing device which is capable of accurately positioning the arm at any desired position by sufficiently balancing the weight of a load head with the force of the spring member coaxially inserted in the arm. The balancing device features compact size, low cost and high operability.

13 Claims, 20 Drawing Figures

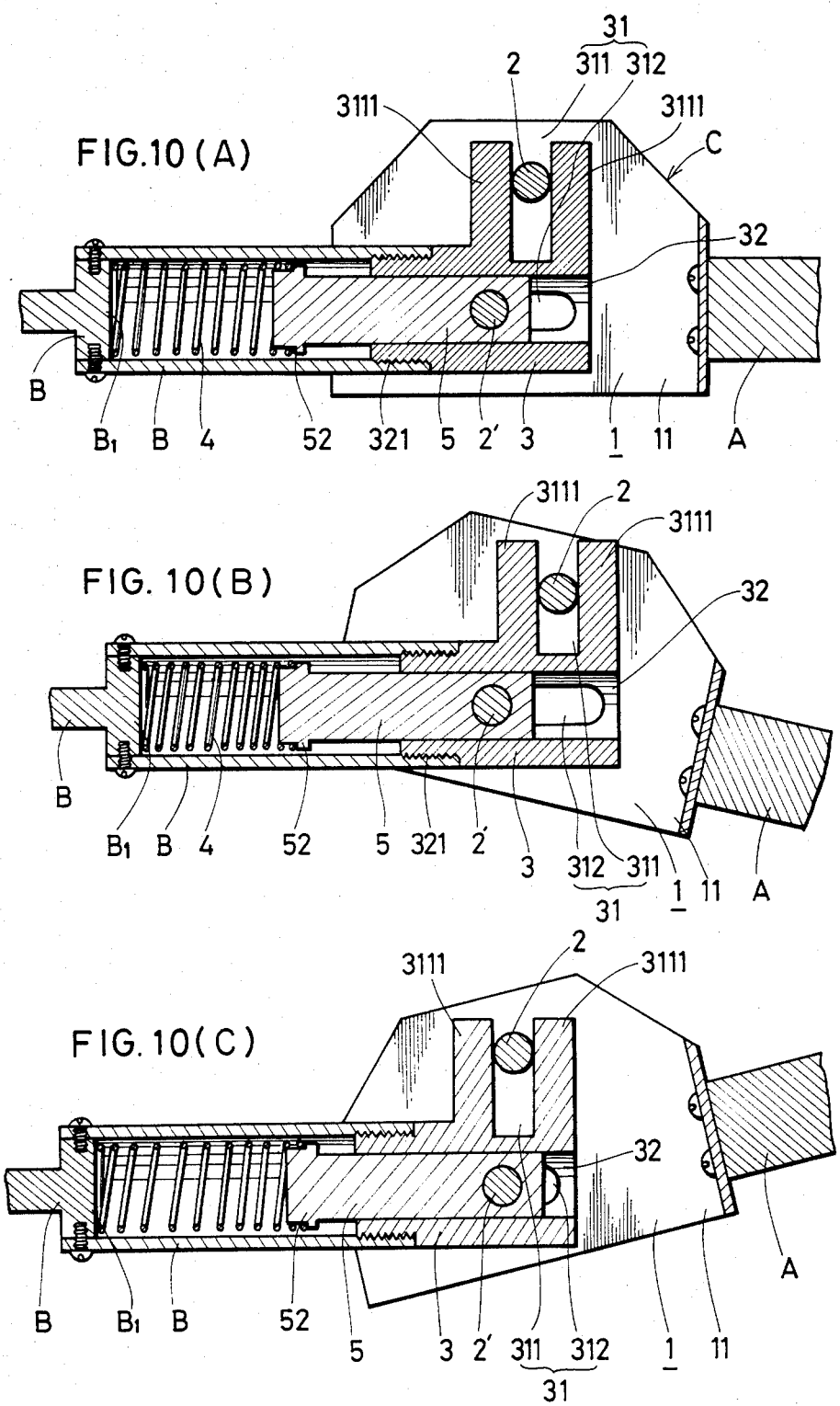

BALANCING DEVICE FOR DENTAL ARM

BACKGROUND OF THE INVENTION

1. Field of the Invention

This invention relates to a balancing device for vertically moving dental arm assembly used for a dental light, dental tray, X-ray source, or the like.

2. Prior Art

A conventional balancing device for a dental light fixed to a moving arm includes a spring as shown in FIGS. 1 (A) and 1 (B). FIG. 1 (A) is a partially cutaway plane view of the balancing device, and FIG. 1 (B) is a sectional view taken along the line Y—Y in FIG. 1 (A). Referring to these figures, a light arm b is connected to a hanger arm through a spring member c so that it can move vertically. With this device, it is impossible to balance the arms a and b by using the restoration force of the spring member c. A wing nut $c_1$ is tightened or loosened to securely position the light arm b. The light arm b is vertically fixed by the friction caused by the tightened wing nut $c_1$. This tightening/loosening, however, is troublesome because the lamp head of the dental light must be moved frequently and positioned accurately. In addition, the movement of the light arm be is not smooth. These are a mental burden to the operator.

A parallel rod type (not shown) is also used for this kind of balancing device. The device of this type has a very high operability, since it is balanced mechanically. However, it is complicated, expensive and larg. If the dental light including this balancing device is placed over the operator and patient, it causes excessive mental pressure and uncomfortableness.

Furthermore, the dental arm swinging device, Japanese Utility Model laid-open No. 57-185114, proposed by the applicant of the present invention, is very useful for a swinging movement with a relatively small rotation moment. However, it is not suited for a balancing device used for a large arm which needs a rotation moment range of 50-80 kgcm.

SUMMARY OF THE INVENTION

It is, therefore, the principal object of the present invention to provide a balancing device which is useful to make a dental arm for a dental light or a tray smaller and less expensive, and to improve the operability of the dental arm. More specifically, the balancing device is characterized in that it is capable of accurate positioning easily and stably using the elasticity of the spring member coaxially inserted in the arm. Embodiments of the present invention are described in detail with reference to the accompanying drawings.

In keeping with the principles of this invention, the objects of the invention are accomplished by a unique structure for a balancing device that comprises: a frame body including a pair of parallel vertical support plates and being connected to the end of a first arm; upper and lower fixed shafts which are horizontal and parallel with each other and are inserted into holes in the support plates; a sliding rod support member which is coaxially connected to the connection end of the second arm and has a crosswise groove and a lengthwise groove whose longitudinal axes intersect into which the fixed shafts are slidably inserted, respectively; a spring member inserted in the connection section of the sliding rod support member and the second arm; and a sliding rod which is supported by either of the fixed shafts and inserted coaxially and slidably into the second arm in the lengthwise direction of the lengthwise groove within the sliding rod support member to continuously apply a force to the spring member. With the structure, a load head moves freely up and down, when the first or second arm is moved, while the movements of the crosswise groove and the lengthwise groove are interrelated with each other and restricted by the fixed shafts. The load head L also stays at any desired position by the restoration force of the spring member.

BRIEF DESCRIPTION OF THE DRAWINGS

FIG. 1 (B) is a sectional view taken along the line Y—Y in FIG. 1 (A);

FIGS. 10 (A), 10 (B), and 10 (C) are vertical sectional views of the second embodiment of the present invention, respectively corresponding to FIGS. 4, 5 and 6;

FIG. 11 (B) is a sectional view taken along the line Y—Y in FIG. 11 (A); and

DETAILED DESCRIPTION OF THE INVENTION

Figure 1A:
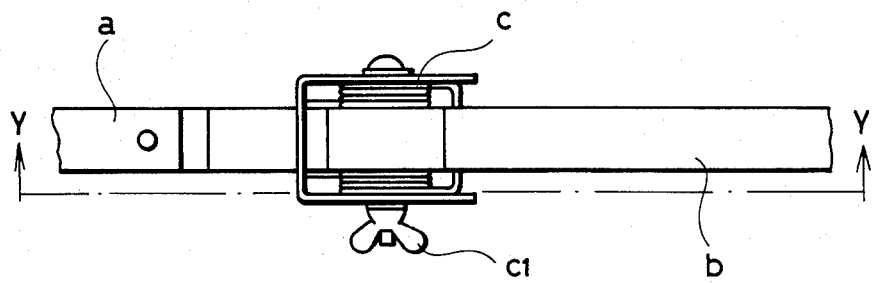
FIG. 1 (A) is a partially cutaway plane view of a balancing device in the prior art.
Figure 1B:
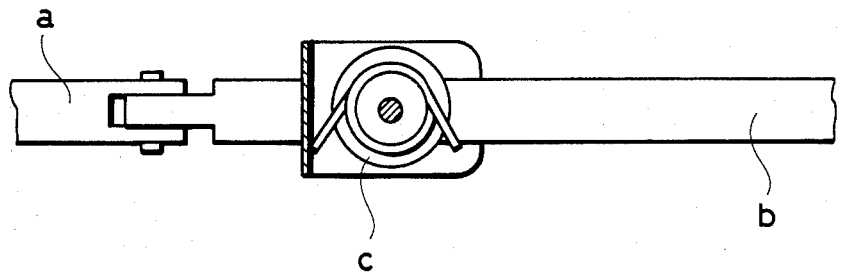

The invention relates to a balancing device for a vertically movable dental arm assembly, adapted to be interposed therein. The dental arm assembly includes arms A, B and a head load L, either of the arm A or B being vertically movable. The balancing device comprises a frame body 1 which includes a pair of parallel vertical support plates 11 and 11, and is connected to the end of the arm A. Two upper and lower fixed shafts 2 and 2', which are horizontal and parallel with each other, are inserted into holes 111 and 111 in the support plates 11 and 11. A sliding rod support member 3, coaxially connected to the connection end of the arm B, has groove means 31 which includes a crosswise groove 311 and a lengthwise groove 312 whose longitudinal axes intersect, in which the fixed shafts 2 and 2' are slidably inserted, respectively. A spring member 4 is housed in the connection section of the sliding rod support member 3 and the arm B. A sliding rod 5 is supported by either of the fixed shaft 2 or 2' and inserted coaxially and slidably into the arm B in the lengthwise direction of the lengthwise groove 312 in the sliding rod support member 3 to continuously apply a force to the spring member 4. With the above structure, load head L can be moved freely up and down, when the arm A or B is moved, while the movements of the crosswise groove 311 and the lengthwise groove 312 are interrelated with each other and restricted by the fixed shafts 2 and 2'. The load head L also can be stopped stably at any desired position by the restoration force of the spring member 4.

Figure 2:
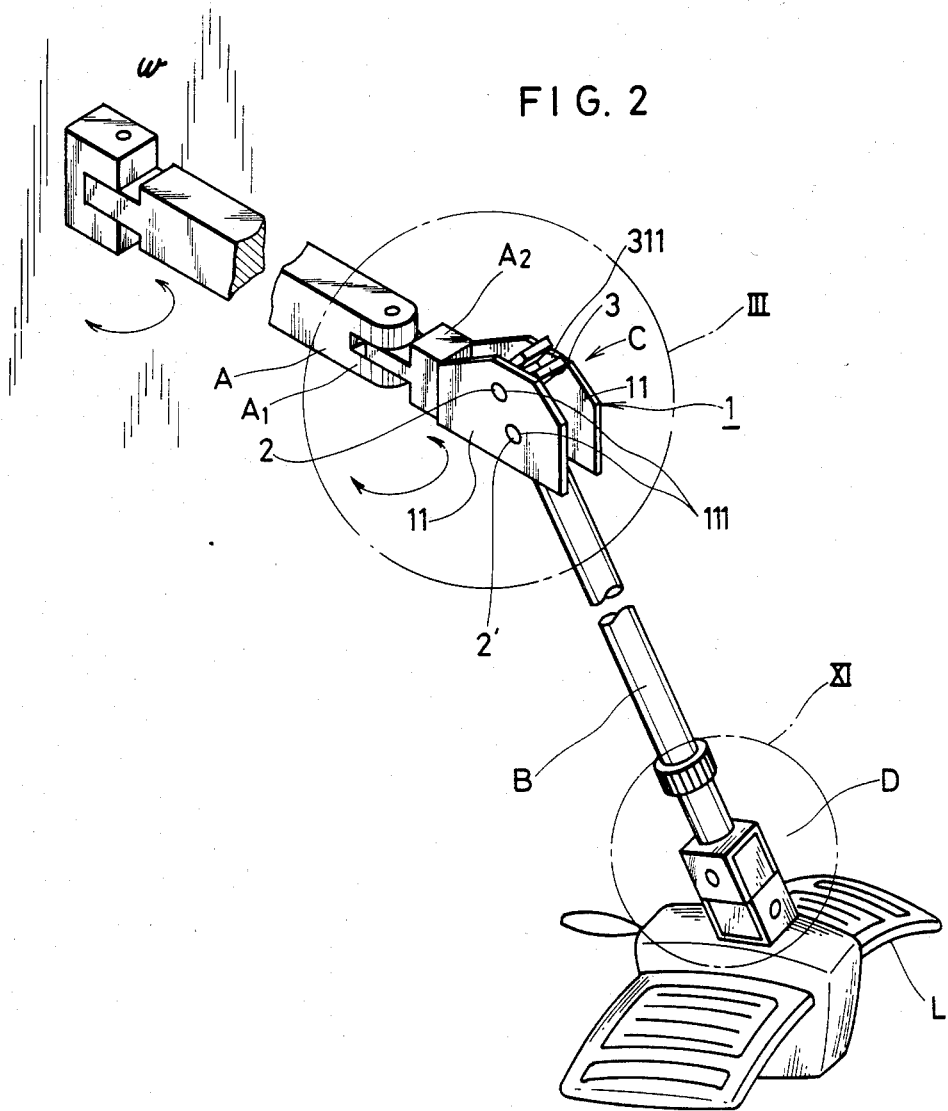
FIG. 2 is a partially cutaway perspective view showing the first embodiment of a dental light using the balancing device of the present invention.

FIG. 2 shows the first embodiment of the present invention, i.e., an application to a dental light.

The balancing device C of the present invention is connected, movably in the horizontal direction, to the end of a hanger arm A which is installed, movably in the horizontal direction, on a wall surface w.

A light arm B is also connected to the balancing device C. A load head, that is, a lamp head L, is connected to the end of the light arm B through a swinging device D described later. The frame body 1 of the balancing device C has a U-shaped cross section and is supported by a connector A2 which is connected to the end of the hanger arm A by a bracket A1. The upper and lower fixed shafts 2 and 2', which are horizontal and parallel with each other at different levels, are inserted into holes in the parallel support plates 11 and 11 of the frame body 1 and are fixed by screws. The lower fixed shaft 2' must be installed perpendicular to the axis of the light arm B. Furthermore, it is preferable that the center of the fixed shaft 2' is located away from the center of the fixed shaft 2 toward the light arm B to maintain an effective balance as described later.

The lower section of the sliding support member 3 has a lengthwise groove 312 and a circular hole 32 which intersects the groove 312 and can slidably accommodate the sliding rod 5 in the axial direction of the light arm B. Around the exterior of the circular hole 32, a male thread 321 is provided coaxially to the circular hole 32 so that it can be connected to the light arm B.

In addition, at the upper section of the sliding rod support member 3 is provided with a crosswise groove 311 which is perpendicular to the lengthwise groove 312. According to the drawings, the upper section of the crosswise groove 311 is open. Therefore, the crosswise groove 311 is composed of two parallel groove walls 3111 and 3111.

At one end of the sliding rod 5, a circular hole 51, perpendicular to the axis of the rod, is provided, into which the fixed shaft 2' is inserted. At the other end, a flange 52 is formed to support and position the spring member 4 and to prevent the sliding rod 5 from excessively entering the circular hole 32. The spring member 4 is a compression spring. A stopper B1 is provided in the proper position inside the light arm B to support and position the spring member 4.

Figure 3:
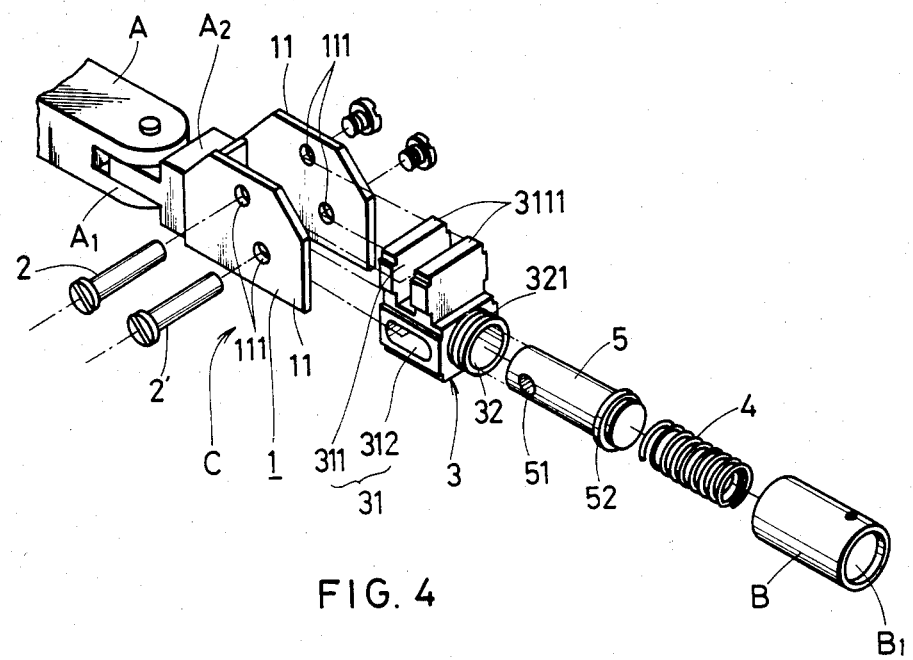
FIG. 3 is an enlarged exploded perspective view of the circled portion III in FIG. 2.

The balancing device C having the structure described above is assembled as below. Referring to FIG. 3, the sliding rod 5 together with the spring member 4 is inserted into the left end of the light arm B. The light arm B is screwed to fix the male thread 321 of the sliding rod support member 3 with compressing the spring member 4 and applying the spring force to the sliding rod 5. Next, the sliding rod support member 3 is inserted in the space between the support plates 11 and 11 of the frame body 1. The upper fixed shaft 2 is inserted into small holes 111 and 111, which are provided in the support plates 11 and 11, by passing the shaft through the crosswise groove 311, and is fixed to the outside of the support plate. In the same way, the lower fixed shaft 2' is inserted into small holes 111 and 111 by passing the shaft 2' through the lengthwise groove 312 and the circular hole 51 in the sliding rod 5. The shaft 2 is fixed with a screw at the outside of the support plate 11. As described above, the balancing device C of the present invention is completely assembled.

Figure 11A:
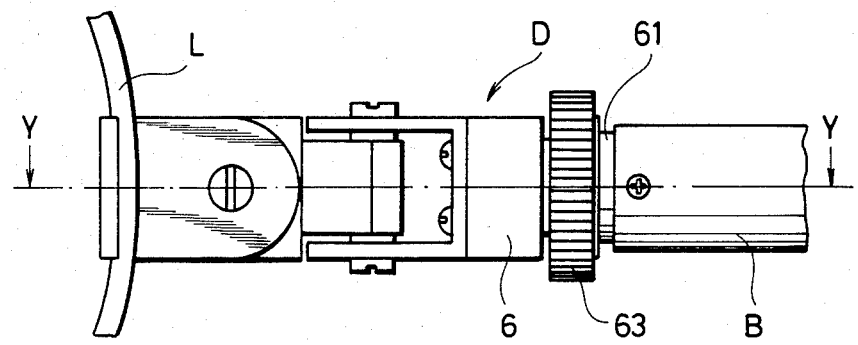
FIG. 11 (A), is a plane view of the circled portion XI in FIG. 2.
Figure 11B:
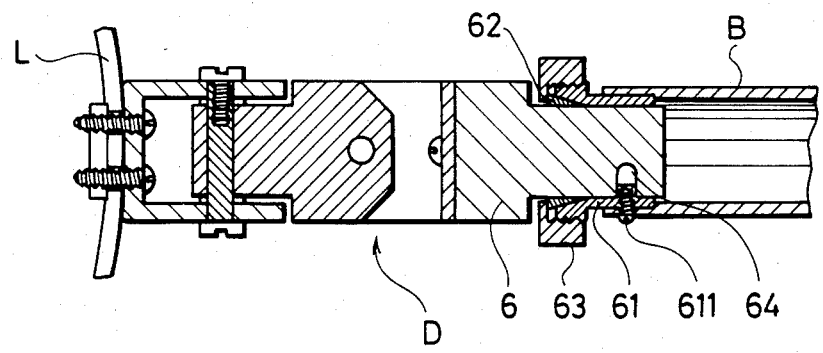

When this balancing device is practically used as a dental light, it is obvious that the swinging device D and the light head L are installed at the end of the light arm B. These devices are further described referring to FIG. 2, FIG. 11 (A) and FIG. 11 (B).

The swinging device D, located between the end of the light arm B and the lamp head L, is composed of a universal joint which can freely move in the horizontal and vertical directions and rotate around the axis of the light arm B. The movement of the swinging device in the horizontal and vertical dirctions are obvious from the figures.

The movement around the axis will be detailed below. The insertion end of a joint body 6 is inserted into the end of the light arm B in which a threaded collar 61 is fixed with a screw 611, and is pressure-fit in the collar 61 by the engagement between a female thread ring 63 and the male thread on the collar 61 through a tapered collar 62. Since the tapered collar 62 is used when the ring 63 is engaged with the collar 61, the joint can freely rotate around the axis of the light arm B of the lamp head L and stop stably at any desired position by adjusting the engagement tightening force. The insertion section of the joint body 6 is provided with a groove 64 into which is screwed the screw 611 to prevent the joint body 6 from extracting from the light arm B.

Figure 4:
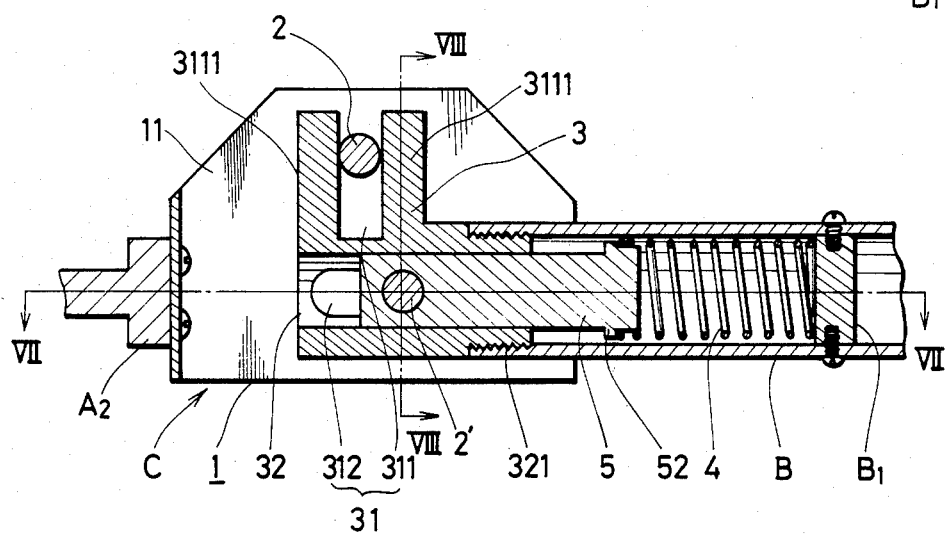
FIGS. 4, 5 and 6 are vertical sectional views showing the operational conditions of the balancing device.
Figure 9A:
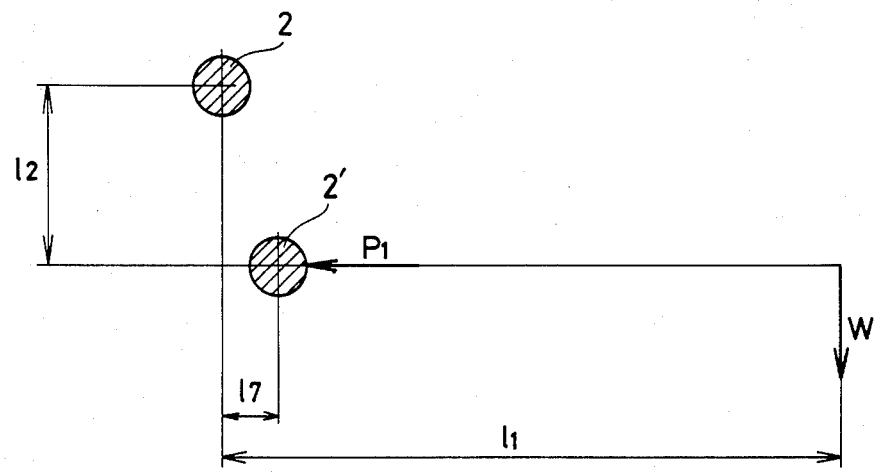
FIGS. 9 (A), 9 (B) and 9 (C) are dynamical explanation figures respectively corresponding to FIGS. 4, 5 and 6.
Figure 9:
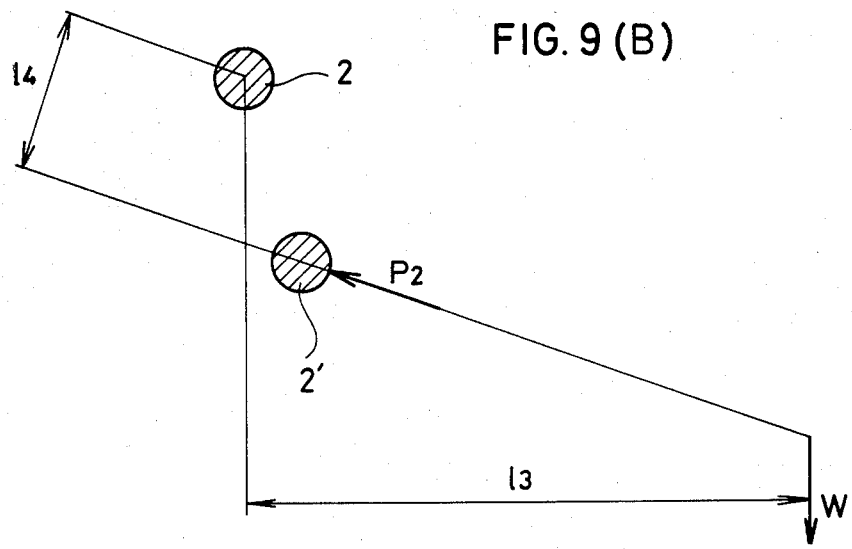
Figure 9:
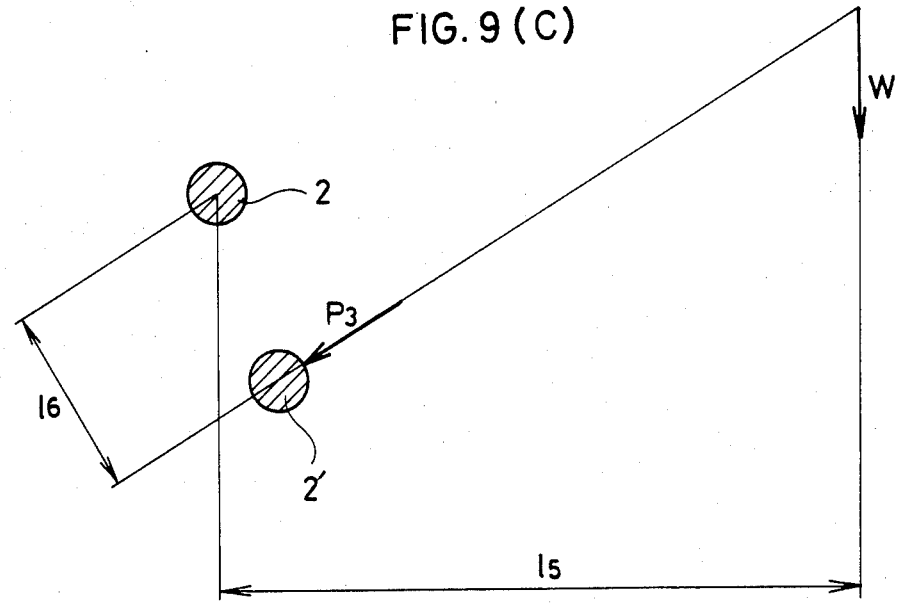

Next, the functions of the dental light having the construction described above will be described. FIG. 4 shows the condition when the lamp head L is horizontal. FIG. 9 (A) is the dynamical explanation figure of the condition.

When the total weight of the light arm B, device D and lamp head L is W, the horizontal distance from the upper fixed shaft 2 and an action point is $l1$, the restoration force of the spring member 4 against the lower fixed shaft 2' is P1, and the vertical distance from the fixed shaft 2 to the axis line of the light arm B is $l2$, and if these factors are determined to satisfy the moment equation of $l1 \times W = l2 \times P1$, the light head L is balanced as shown in FIG. 4.

Figure 5:
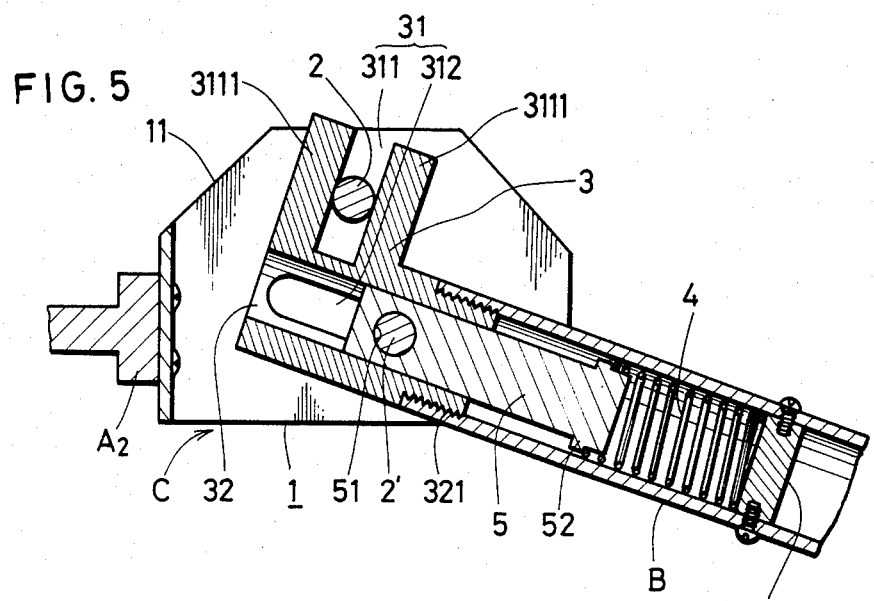

When the lamp head L is pushed downward as shown in FIG. 5, the crosswise groove 311 slides upward along the fixed shaft 2, thus the lengthwise groove 312 also slides to the hanger arm A. As a result, the sliding rod support member 3 rotates clockwise, while the movements of the crosswise groove 311 and the lengthwise groove 312 are interrelated with each other and restricted by the fixed shafts 2 and 2'. Since the sliding rod 5 is supported by the fixed shaft 2' at this time, as the lengthwise groove 312 slides to the hanger arm A, the sliding rod 5 moves apparently to the light arm B and additionally compresses the spring member 4.

FIG. 9 (B) is the dynamical explanation figure of the above condition. When the horizontal distance from the action point to the fixed shaft 2 is $l2$, the vertical distance from the fixed shaft 2 is to the light arm B is $l4$, and the restoration force of the spring member 4 against lower fixed shaft 2' is P2, the moment equation of $l2 \times W = l4 \times P2$ must be satisfied to balance the light head L. Since P2 is related to the compression degree of the spring member 4, this equation can be satisfied by selecting the off-center distance $l7$ between the fixed shafts 2 and 2' in the horizontal direction (in FIG. 9 (A)) and the spring coefficient of the spring member 4. Even when the rotation moment of the light is great, a moment which is enough to cope with the great moment is obtained, if the value of l7 is large.

Figure 6:
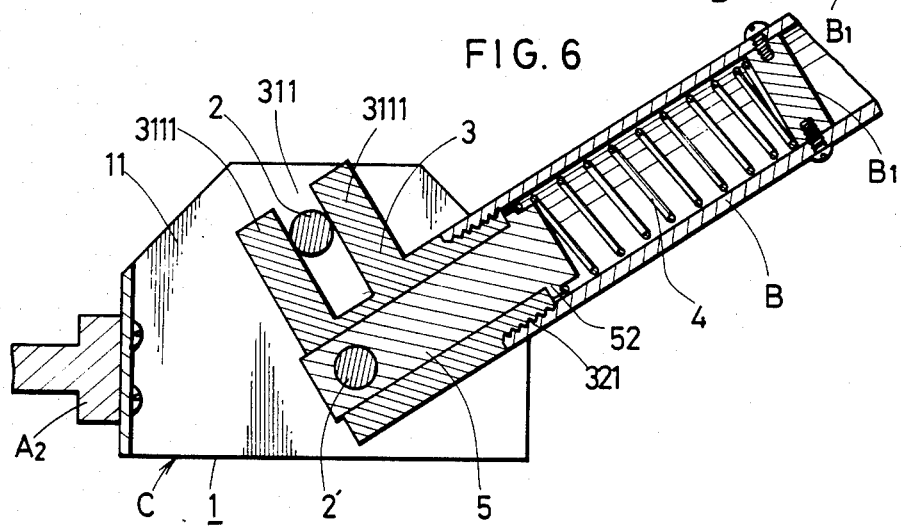
Figure 7:
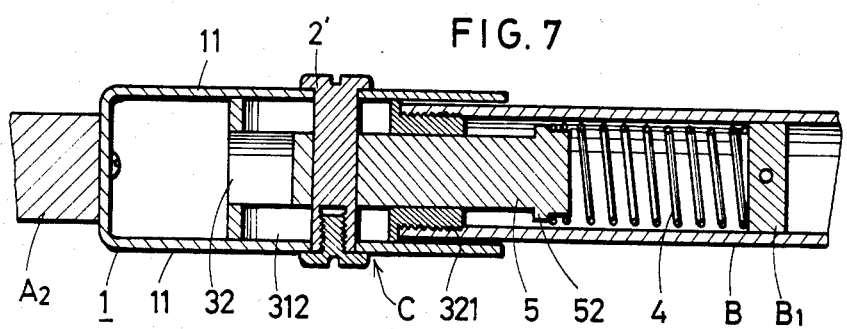
FIG. 7 is a sectional view taken along the line VII-—VII in FIG. 4.
Figure 8:
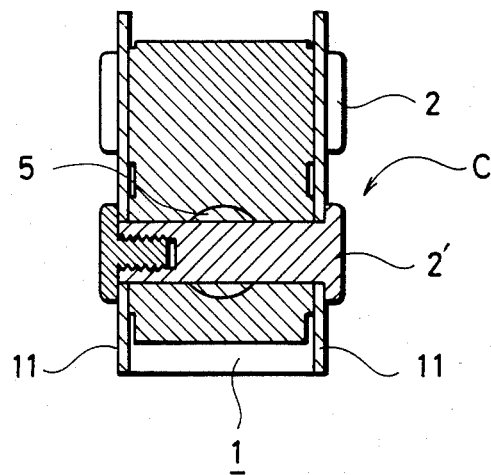
FIG. 8 is a sectional view taken alond the line VIII-—VIII in FIG. 4.

Furthermore, if the lamp head L is pushed upward from the horizontal position as shown in FIG. 6, the sliding rod support member 3 rotates counterclockwise, opposite to the direction in the case shown in FIG. 5. As the lengthwise groove 312 slides to the light arm B, the sliding rod 5 apparently moves to the hanger arm B. As a result, the spring member 4 extends and the spring force against the sliding rod 5 becomes weak.

FIG. 9 (C) is the dynamical explanation figure of this condition. When the horizontal distance from the action point to the fixed shaft 2 is l5, the vertical distance from the fixed shaft 2 and the axis of the light arm B is l6, and the restoration force of the spring member 4 is P3, the moment equation of $l5 \times W = l6 \times P3$ must be satisfied to balance the light head L as described above. By properly selecting l2, l7 and the spring coefficient of the spring member 4 so that the above three moment equations are almost satisfied, the lamp head L can be held stably in any position in its moving range.

As clearly explained in the above descriptions regarding the construction and the functions, the balancing device of the above embodiment of the present invention is constructed such that the spring member 4, a means to keep balance, is inserted in the cylindrical light arm B, the crosswise and lengthwise grooves 311 and 312 in the sliding rod support member 3 slide along the fixed shafts 2 and 2' installed in the frame body 1 while the movements of the two grooves are interrelated with each other and restricted by the fixed shafts 2 and 2'.

Therefore, the lamp head L can freely move in the vertical direction toward the hanger arm A. Thus, the lamp head L can be stably held at any desired position with great ease.

In addition, the device has a simple and compact construction. Furthermore, even when a large rotation moment is applied to the lamp head L, this moment can be coped with by selecting the proper arrangement relationship between the fixed shafts 2 and 2' and the spring coefficient of the spring member 4. Consequently, the balancing device is best suited for dental lights and the similar equipment.

FIGS. 10 (A), 10 (B) and 10 (C) show the second embodiment of the present invention. In this embodiment, the relationship between the balancing device C and the arms A and B is opposite to that in the above description. In other words, the arm A is located at the movable side, and the arm B is located at the stationary side. In this respect, the second embodiment differs from the first embodiment. Accordingly, this balancing device is dynamically opposite to the balancing device of the first embodiment. It is obvious that the center of the lower fixed shaft 2' should be located away from the center of the upper fixed shaft 2 toward the hanger arm B to obtain stable balance, according to the previous description. It is needless to mention that the moving performance of the lamp head L in the vertical direction and the basic dynamical principle to keep balance are identical with the previous description.

Figure 12A:
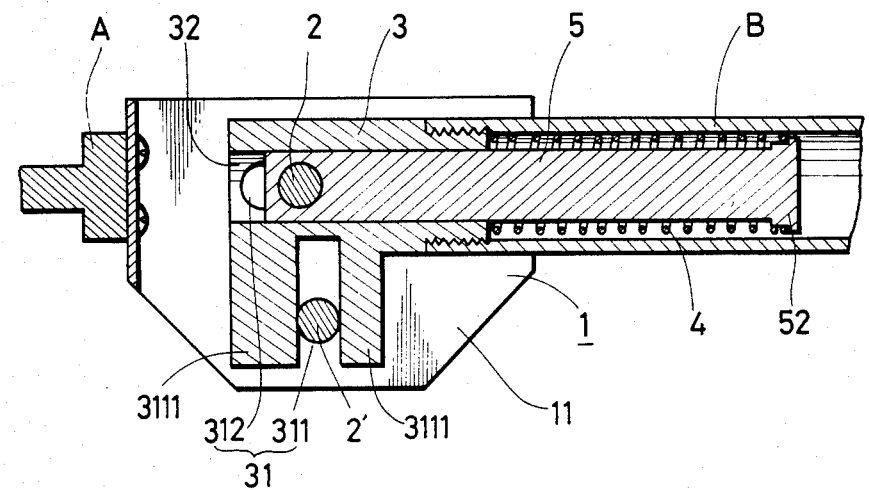
FIGS. 12 (A), 12 (B) and 12 (C) are vertical sectional views of the third embodiment of the present invention, respectively corresponding to FIGS. 4, 5 and 6.
Figure 12B:
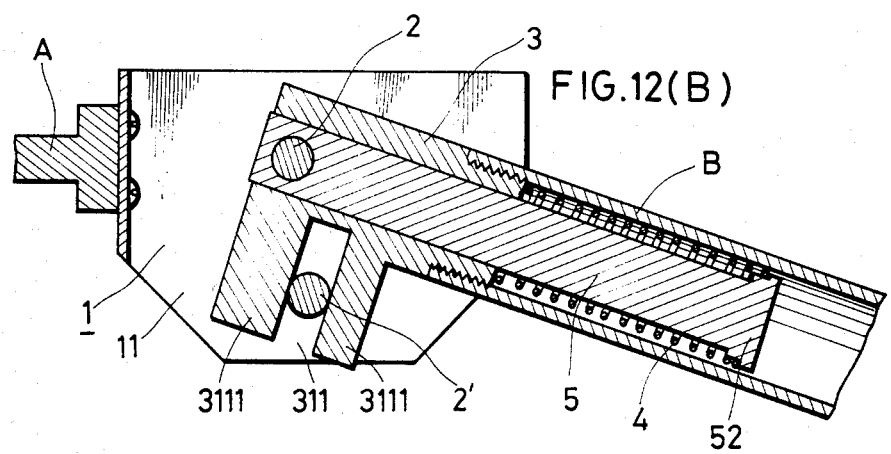
Figure 12C:
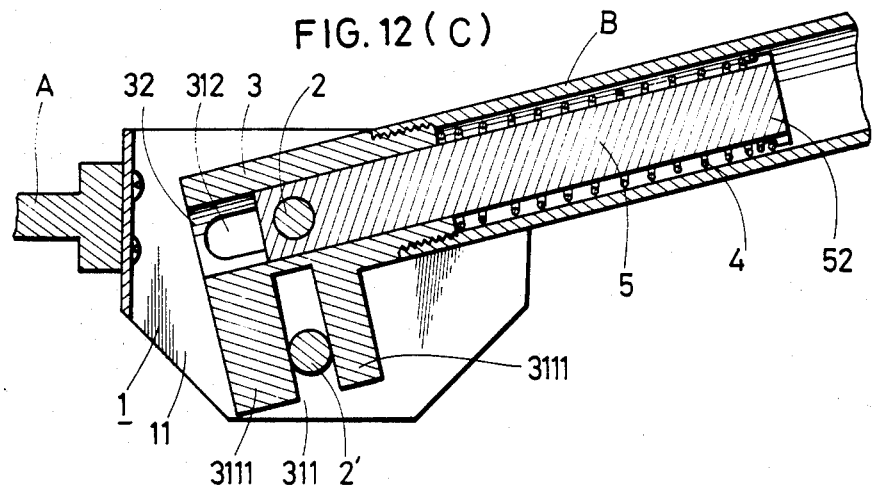

FIGS. 12 (A), 12 (B) and 12 (C) show the third embodiment of the present invention. The relationship between the sliding rod support member 3 and the fixed shafts 2 and 2' is reversed in the vertical direction. Accordingly, the spring force direction of this embodiment should be opposite to that of the first embodiment, and a tension spring should be used instead of a compression spring. However, the structure of the third embodiment is improved by changing the spring fixing method and the assembly method of the balancing device so that a compression spring can be used. It is also needless to mention that the moving performance of the lamp head L in the vertical direction and the basic dynamical principle to keep the balance are identical with the previous description.

Although a dental light is used in the description of the embodiments, it is obvious that the present invention is not limited to a dental light but preferably applicable to a tray arm (the load head is a tray), an X-ray photographing arm (the load head is an X-ray generator), or the like. It is needless to mention that this invention is applicable to the poll type and the suspension type of a dental light, although the dnetal light in the previous description is installed on the wall. In addition, although the upper section of the crosswise groove 311 in the sliding support member 3 is open, it can be closed at its both ends in the same way as those of the lengthwise groove 312 as required.

Furthermore, the groove in the sliding rod support member have circular arc or curved shapes instead of straight-line shapes as required, provided that no dynamical problem is caused.

As mentioned above, the balancing device of the present invention has a large resistance to cope with large moments, yet freely movable in the vertical direction, although it is compact. Therefore, this device is best suited for equipment such as a dental light wherein the rotation moment at the lamp head is great and the lamp head must be moved frequently and positioned accurately.

The conventional balancing devices are large and expensive, or they are troublesome to perform accurate positioning, causing mental burden. The balancing device of the present invention is free from these drawbacks.

Furthermore, the dental light can have greater practical performance by using the above-mentioned swinging device between the lamp head and the lamp arm, together with the balancing device. In this way, this invention has significant advantages.

Having described our invention as related to the embodiments shown in the accompanying drawings, it is our intention that the invention be not limited by any of the details of description, unless otherwise specified, but rather be construed broadly within its spirit and scope as set out in the accompanying claims.

We claim:

1. A balancing device for a vertically movable dental arm assembly, which includes first and second arms and a head load, either of said arms being vertically movable, characterized in that said balancing device comprises:

a frame body which includes a pair of parallel vertical support plates and is connected to the end of said first arm;

upper and lower fixed shafts which are horizontal and parallel with each other at different levels and are inserted into holes in said support plates;

a sliding rod support member which is coaxially connected to the connection end of said second arm and has a crosswise groove and a lengthwise groove whose longitudinal axes intersect into which said fixed shafts are slidably inserted respectively;

a spring member inserted in the connection section of said sliding rod support member and said second arm; and a sliding rod which is supported by either of said upper and lower fixed shafts and inserted coaxially and slidably into said second arm in the lengthwise direction of the lengthwise groove within said sliding rod support member to continuously apply a force to said spring member;

whereby said load head moves freely up and down when said first or second arms is moved, while the movements of said crosswise groove and lengthwise groove are interrelated with each other and restricted by said fixed shafts, and said load head is positioned at any desired position by the restoration force of said spring member.

2. A dental arm balancing device as claimed in claim 1, wherein said load head is a lamp head.

3. A dental arm balancing device as claimed in claim 1, wherein said load head is a dental tray.

4. A dental arm balancing device as claimed in claim 1, wherein said load head is an X-ray generator.

5. A dental arm balancing device as claimed in claim 1, wherein said first arm is stationary and second arm is movable.

6. A dental arm balancing device as claimed in claim 1, 2, 3, 4 or 5, wherein said second arm is movable, and said sliding rod is supported by said lower fixed shaft, of which the center is located away from the center of said upper fixed shaft toward said second arm.

7. A dental arm balancing device as claimed in claim 1, 2, 3, 4 or 5, wherein said second arm is movable, and said sliding rod is supported by said upper fixed shaft, of which the center is located away from the center of said lower fixed shaft toward said first arm.

8. A dental arm balancing device as claimed in claim 1, wherein said first arm is movable and second arm is stationary.

9. A dental arm balancing device as claimed in claim 1, 5 or 8, wherein said load head is a lamp head, said lamp head being connected to the end of said first or second movable arm through a swinging device.

10. A dental arm balancing device as claimed in claim 9, wherein said second arm is movable, and said sliding rod is supported by said lower fixed shaft, of which the center is located away from the center of said upper fixed shaft toward said second arm.

11. A dental arm balancing device as claimed in claim 9 wherein said second arm is stationary, and said sliding rod is supported by said lower fixed shaft, of which the center is located away from the center of said upper fixed shaft toward said second arm.

12. A dental arm balancing device as claimed in claim 9, wherein said second arm is movable, and said sliding rod is supported by said upper fixed shaft, and the center of said upper fixed shaft is located away from the center of said lower fixed shaft toward said first arm.

13. A dental arm balancing device as claimed in claim 1, 2, 3, 4 or 8, wherein said second arm is stationary, and said sliding rod is supported by said lower fixed shaft, of which the center is located away from the center of said upper fixed shaft toward said second arm.

* * * * *